| United States Patent [19] | [11] Patent Number: 5,013,665 |
| Suzuki et al. | [45] Date of Patent: May 7, 1991 |

[54] METHOD FOR REGENERATING DEACTIVATED MICROORGANISMS

[75] Inventors: Motoshi Suzuki, Kenilworth; Howard Dalton; Anthony O. Richards, both of Leamington Spa; Stephen H. Stanley, Kenilworth, all of United Kingdom

[73] Assignee: Idemitsu Kosan Company Limited, Tokyo, Japan

[21] Appl. No.: 273,367

[22] Filed: Nov. 17, 1988

[51] Int. Cl.$^5$ .......................... C12N 1/12; C12N 1/38
[52] U.S. Cl. .................................... 435/244; 435/247; 435/250; 435/252.1; 435/252.34; 435/858; 435/859; 435/863
[58] Field of Search ................ 435/244, 252.1, 252.34, 435/247, 250

[56] References Cited

U.S. PATENT DOCUMENTS

| 3,419,473 | 12/1968 | Dawson | 435/252.1 |
| 3,755,082 | 8/1973 | Terui et al. | 435/247 |
| 4,042,458 | 8/1977 | Harrison et al. | 435/247 |
| 4,048,017 | 9/1977 | Roesler | 435/247 |
| 4,106,988 | 8/1978 | Ohsugi et al. | 435/247 |
| 4,266,034 | 5/1981 | Patel et al. | 435/247 |
| 4,348,476 | 9/1982 | Hou | 435/123 |
| 4,368,267 | 1/1983 | Hou et al. | 435/250 |
| 4,425,432 | 1/1984 | Zeikus et al. | 435/247 |
| 4,587,216 | 5/1986 | Patel et al. | 435/123 |
| 4,594,324 | 6/1986 | Dalton et al. | 435/123 |
| 4,782,024 | 11/1988 | Scott et al. | 435/247 |
| 4,795,708 | 1/1989 | Sperl et al. | 435/247 |

*Primary Examiner*—Herbert J. Lilling
*Attorney, Agent, or Firm*—Frishauf, Holtz, Goodman & Woodward

[57] ABSTRACT

The present invention relates a method for reactivating or regenerating the methane oxidizability of a methane-utilizing bacteria which have partly or wholly lost its methane oxidizability by culturing said methane-utilizing bacteria in a specified condition, and further relates to a method for continuous production of oxides by bringing a methane-utilizing bacteria in contact with alkanes, alkenes or cyclic compounds.

19 Claims, 2 Drawing Sheets

METHOD FOR REGENERATING DEACTIVATED MICROORGANISMS

FIELD OF THE INVENTION

The present invention relates to a method for the reactivation of deactivated microbial cells and, more particularly, to a method for the reactivation of a methane-utilizing bacteria which have partly or wholly lost its methane oxidizability, by reactivating it in a reactivation solution to which a specific substance is added.

BACKGROUND OF THE INVENTION

The methane oxidation enzymes (methane monooxygenase) which methane-utilizing bacteria possess can oxidize not only methane but also alkanes, alkenes, cyclic compounds, organic sulfur compounds and organic nitrogen compounds to the corresponding oxides and are of high industrial value, but have the disadvantage that they tend to be easily deactivated due to their poor stability. If the methane oxidizability of deactivated microorganisms can be reactivated, it is then possible to repeatedly use the microbial cells and, hence, cut down the production cost. Until now, it has been known to regenerate the methane oxidizability of deactivated microbial cells by the supply of a carbon source and oxygen. However, any satisfactory results are not still obtained (U.S. Pat. No. 4,348,476).

For that reason, the present inventors have made intensive and extensive studies with a view to reactivating the methane oxidizability of deactivated microorganisms to a sufficient level, thereby making it possible to use them repeatedly. In consequence, the present inventors have found a method capable of regenerating the methane oxidizability of deactivated microorganisms by regenerating them in a reactivation solution to which a specific substance is added, and have accomplished the present invention.

SUMMARY OF THE INVENTION

The first of the present invention provides a method for reactivating the methane oxidizability of a methane-utilizing bacteria which have partly or wholly lost its methane oxidizability, characterized in that said methane-utilizing bacteria is cultured in an reactivation solution containing at least one of methane, methanol and formaldehyde, while supplying thereto a nitrogen source, a sulfur source and oxygen.

The second of the present invention provides a method for regenerating the methane oxidizability of a methane-utilizing bacteria which have partly or wholly lost their methane oxidizability, characterized in that said methane-utilizing bacteria are cultured with supplying oxygen and a methionine derivative thereto, and the third of the present invention provides a method for the continuous production of oxides which comprises producing oxides by bringing methane-utilizing bacterial in contact with alkanes, alkenes or cyclic compounds in the presence of an electron donor in a reactor vessel, discharging the resulting oxides from the system to the outside, regenerating said methane-utilizing bacteria having decreased methane oxidizability in a regenerating vessel to recover said methane oxidizability, and then returning said bacteria to the reactor vessel for the production of said oxides.

DETAILED DESCRIPTION OF THE INVENTION

Figure 1:
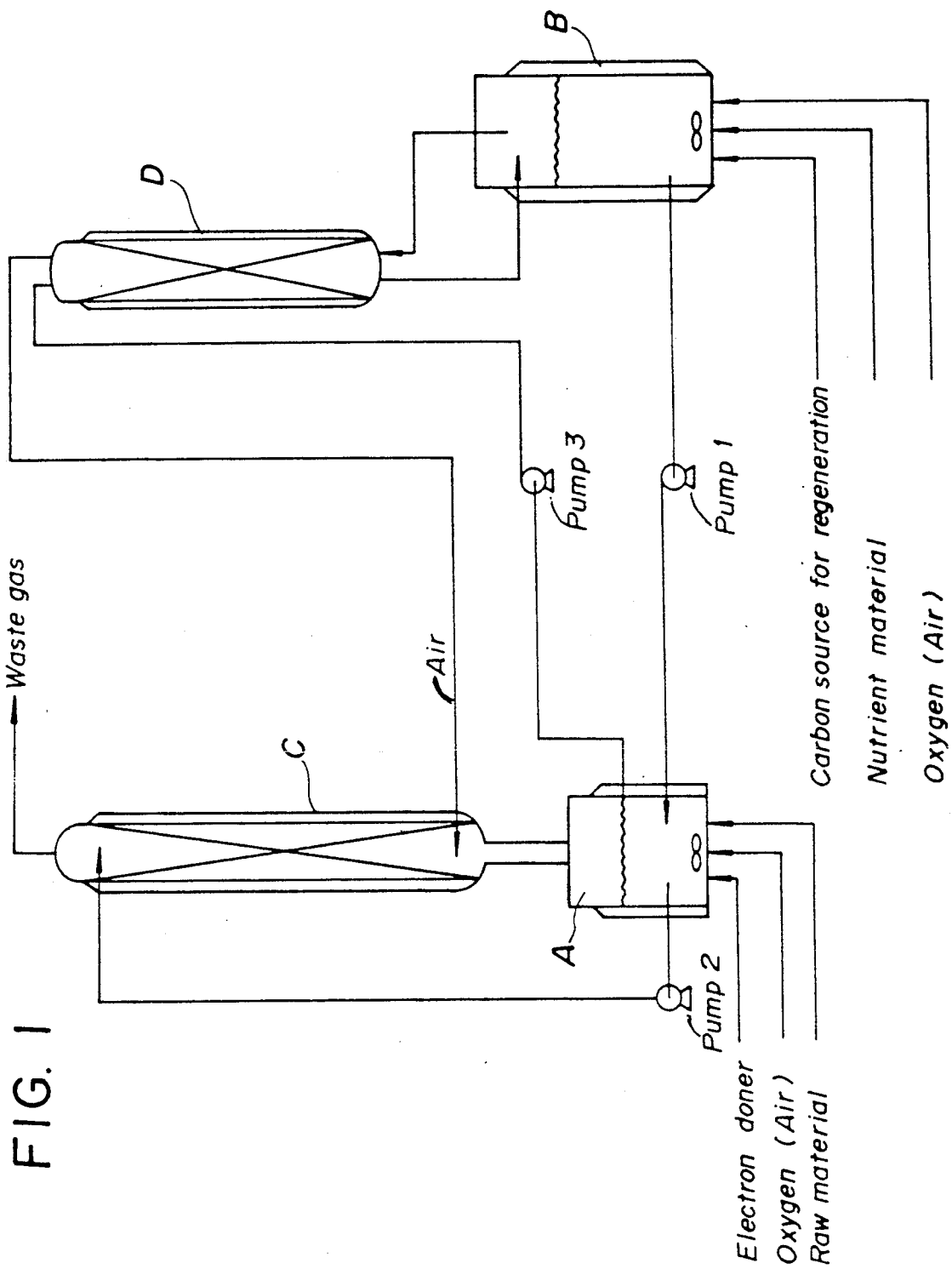
FIGS. 1 and 2 each are a flow sheet illustrating the embodiments of the apparatus systems used for carrying out the method of the present invention.
A: Reactor Vessel
B: Regenerating Vessel
C, D: Scrubbers

An oxidation reaction making use of methane-utilizing bacteria is generally carried out by bringing a starting material into contact therewith in the presence of an electron donor.

As the methane-utilizing bacteria usable in the present invention, there are such microorganisms belonging to genera Methylococcus such as *Methylococcus capsulatus* NCIB 11132, Methylomonas such as *Methylomonas agile* NCIB 11124, Methylosinus such as *Methylosinus trichlosporium* NCIB 11131, Methylocystis such as *Methylocystis parvus* NCIB 11129, Methylobacter such as *Methylobacter capsulata* NCIB 11128 and Methylobacterium such as *Methylobacterium organophilum* ATCC 27886.

The media used for culturing the aforesaid methane-utilizing bacteria may be such that they permit sufficient propagation of said bacteria, and methane, methanol and the like may usually be used as the carbon source. The nitrogen source used may be ammonium chloride, pottasium nitrate, ammonium nitrate and the like which are ordinarily used in the prior art. Besides, phosphates, calcium salts, magnesium salts and slight amounts of inorganic salts (cupric salts, ferrous salts, cobalt salts, etc.) may optionally be added. Preferably, use may be made of a culture medium by Whittenbury et al. (J. Gen. Microbiol., 61, pp. 205-208, 1970). A culture vessel having therein a culture medium is internally replaced by a mixed gas of methane and an oxygenous gas (air, etc.), and the methane-utilizing bacteria are inoculated into the culture medium in contact with said gas.

The methane-utilizing bacteria are aerobic microorganisms, and may be batchwisely or continuously cultured at 15° to 60° C., preferably 20° to 50° C. under aerobic conditions.

The cultured product may be used as such for the oxidation of the raw materials to be described later. However, microbial masses obtained by solid/liquid separation by means of centrifuging, etc. may be used. Further, the obtained microbial masses may be washed with and suspended in a suitable solution such as a phosphate buffer for use. For use, the microbial masses may also be immobilized in the conventional manner.

It is required that, in a reaction tank, the aforesaid methane-utilizing bacteria be brought into contact with the raw material in the presence of an electron donor. The electron donor used includes methane; lower alcohols such as methyl alcohol or ethyl alcohol; α,ω-diols such as ethylene glycol or 1,4-butanediol; lower aldehydes such as formaldehyde, acetoaldehyde or propionaldehyde, formates such as formic acid or sodium formate; hydrogen; $NADH_2$; $NADPH_2$ and methane. These may be used alone or in combination.

The raw materials used may include alkanes such as methane, ethane, propane, butane, hexane, octane and the like; alkenes such as ethylene, propylene, butenes and the like; cyclic compounds such as cyclohexane, benzene, toluene and the like and their derivatives (for instance, halogen-, nitro- and amino-substituted derivatives, alcohols, ethers and esters).

The catalytic oxidation reactions of the raw materials with the methane-utilizing bacteria may be carried out in the presence of electron donors, and the reaction temperature and time may be determined in such a manner that the desired oxidation reactions occur satisfactorily, taking the types of the raw materials and methane-utilizing bacteria into consideration. The reaction conditions may generally be pH 5.5 to 9.0, preferably 6.0 to 8.5 and a temperature of 15° to 60° C., preferably 20° to 50° C.

The corresponding epoxides, alcohols, aldehydes, S-oxides, N-oxides and the like are produced by these oxidation reactions.

It is required to rapidly remove the resulting oxide from within the reactor vessel For instance, a part of the microorganism-containing reaction mixture is introduced into a product collector such as a scrubber, an extractor or a membrane separator to remove the oxide. The whole or a part of the reaction mixture, from which the oxide has been removed, is returned to the reactor vessel.

The methane-utilizing bacteria used in the oxidation reactions as mentioned above partly or wholly lose their methane oxidizability upon repeated use, resulting in deactivated microbial cells. Such microbial cells cannot be re-used directly for the oxidation reactions. In order to regenerate or reactivate the microorganisms which have lost their methane oxidizability, the first method, the microorganisms which have lost their methane oxidizability are taken out of the reaction vessel and supplied to the regenerating vessel, thereafter, the regeneration or reactivation operation may be carried out, while supplying thereto a carbon source, a nitrogen source, a sulfur source and oxygen. The carbon sources to be used include methane, methanol and formaldehyde, which may be used alone or in combination. The amount of methanol or formaldehyde added is in a range of 10 to 600 nmol per minute.mg of microbial cells, preferably 30 to 400 nmol/min..mg of microbial cells. Methanol or formaldehyde may be supplied at once or continuously. However, it is preferred that they should continuously be supplied in suitable amounts. This is because when a large amount of methanol or formaldehyde is added at once, the desired reactivation may not take place due to the development of their toxicity. When methanol or formaldehyde is continuously supplied, the microbial cells may be reactivated even in an amount of below 10 nmol/min..mg of microbial cells, but considerable time is required for that purpose. When methanol or formaldehyde is supplied in an amount of larger than 600 nmol/min..mg of microbial cells, on the other hand, the reactivation of the microbial cells may be interrupted, since it is not completely consumed and accumulated. A mixed gas of methane and air is used, since the methane-utilizing bacteria are aerobes. In this case, the amount of methane to be supplied is equal to or larger than 10 nmol/min..mg of microbial cells, preferably 30 nmol/min..mg of microbial cells. No particular limitation is imposed upon the volume ratio of methane to air. It is understood, however, that the reactivation of microorganisms is retarded in a state extremely deficient in oxygen, and does not take place at all in the absence of oxygen. Too excessive supply of methane may not hinder the reactivation of microorganisms, but results in waste, since the microorganisms cannot consume methane in an amount larger than required. A methane supply rate and a methane/air mixing ratio sufficient to permit consumption of methane in an amount of 30 nmol/min..mg of microbial cells may be used. The nitrogen sources to be used may include inorganic and organic ones such as gaseous nitrogen, nitric acid, potassium nitrate, sodium nitrate, ammonium nitrate, ammonium sulfate, peptone, casaminoic acid, L-glutamine and L-asparagine, which may be added in an amount of not less than 1 nmol/min..mg of microbial cells, preferably in a range of 2 to 500 nmol/min..mg of microbial cells. The reactivation of the microorganism is retarded, when the amount of the nitrogen source is smaller. Excessive addition of the nitrogen source has not any appreciable effect, but may rather inhibit the reactivation of the microorganism.

The sulfur sources to be used may include sulfuric acid, magnesium sulfate, potassium sulfate, sodium sulfate, sodium sulfide, hydrosulfide and sodium sulfhydrate, which may be added in an amount of 0.02 nmol/min..mg of microbial cells or larger, preferably in a range of 0.1 to 150 nmol/min..mg of microbial cells. The activation of microbial cells is retarded, when the amount of the sulfur source is smaller, whereas excessive addition of the sulfur source has not any appreciable effect. These components may continuously be supplied in a certain proportion per a certain time, or may alternatively be added at once in an amount corresponding to several hours at the initiation time of reactivation or in the course of reactivation. When the components are added at once, they may be supplied in an amount corresponding to the amount thereof supplied in the aforesaid continuous manner. When the regeneration of microorganisms carry out, in addition to the above described component sufficient addition of phosphoric acid, magnesium and trace metals may achieve the regeneration of microorganisms simultaneously with the propagation of microorganisms. It is to be noted that an insufficient amount of oxygen results in a delay in the regeneration of microorganisms. The reactivation of microorganism may be carried out by shaking culture at 20° to 50° C. under aerobic conditions, since the methane-utilizing bacteria are aerobes. Although the reactivation temperatures vary with microorganisms, sufficient activation of microbial cells may be achievable in a temperature range in which at least the microbial cells can grow. Although varying depending upon the degree of deactivation, the amounts of the carbon source, nitrogen source, sulfur source and oxygen supplied, temperatures and microorganisms, the time required for reactivation by shaking culture is usually 20 minutes or longer, preferably in a range of 30 to 720 minutes. A longer activation time has not any appreciable effect. The supply of the carbon, nitrogen and sulfur sources in an amount exceeding a sufficient level gives rise to the reactivation of microorganism and, at the same time, the propagation of microorganism. For that reason, two objects, viz., the activation and propagation of microorganism, are achievable in the present invention. The thus reactivated methane-utilizing bacteria can be re-used for the aforesaid oxidation reactions due to their sufficient methane oxidizability.

In the second method for regenerating the microorganisms which have lost their methane oxidizability, in order to regenerate the microbial cells devoid of methane oxidizability, the deactivated microbial cells may be regenerated, while supplying oxygen and a methionine derivative thereto. Preferable for the methionine derivative is a compound expressed by the following formula:

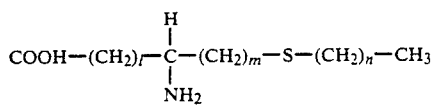

wherein l, m and n stand for 0 or 1, 1-4 and 0 or 1, respectively. The methionine derivatives expressed by Formula (I) include methionine, β-methionine, ethionine, homomethionine and hexomethionine, by way of example.

The methionine derivative may be added to the methane assimilable bacteria in a proportion of 0.02 nmol/-min..mg of cells or higher, preferably 0.05 to 50 nmol/-min..mg of cells, before or after they lose their methane oxidizability, they are reactivated, and the regeneration operation may be carried out at 15° to 60° C. under aerobic conditions for 30 to 600 minutes The methionine derivative may be continuously supplied in a certain proportion for a certain period of time, as mentioned above. Alternately, it may be added all at once in an amount corresponding to specified time at the initiation time or in the course of reactivation.

The thus regenerated methane-utilizing bacteria can be re-used for the aforesaid oxidation reaction due to their sufficient methane oxidizability.

In the third method of the present invention, the methane-utilizing bacteria regenerated are again returned to be reactor vessel for the production of the oxides. In this manner, the oxides can be stably produced for extending over a long time. It is preferred in the present invention that benzoic acid or its metal salt (e.g., its alkaline metal salt or alkaline earth metal salt) is added to the reaction system (the reactor vessel and/or the regeneration vessel) so as to promote the regeneration of the deactivated microbial cells at any time of the process of the present method, e.g., at the time of the feed of the raw material to the reactor vessel or the initiation of the reaction, or during the reaction, or at the time of the regeneration of the microbial cells. The amount of benzoic acid or its metal salt added is suitably in a range of 0.1 to 8 mmol/liter, preferably 0.2 to 5 mmol/liter.

In the production of the oxides, the co-oxidation capability can be increased by controlling the concentration of carbonic acid ions in the reaction solution. Concretely, carbon dioxide and/or inorganic carbonates are added to the reaction system. When carbon dioxide is used, it is preferably added as a mixed gas of air and carbon dioxide (1/0.1 to 1/0.75 by volume). Since the pH of the reaction solution drops on adding carbon dioxide, it is necessary for the carbon dioxide to be added thereto while maintaining the pH of the reaction solution in the range of 5.5 to 9.0 by neutralizing with a basic substance such as potassium hydroxide, sodium hydroxide and ammonia. Representative examples of inorganic carbonates are potassium carbonate, sodium carbonate, sodium hydrogencarbonate and ammonium carbonate. The inorganic carbonate is added in a proportion of 1 to 140 mmol/l preferably 1 to 130 mmol/l although the optimum amount somewhat varies with the type of the strain used.

According to the present invention, the alcohol, epoxide or cyclic alcohol corresponding to the raw material can be obtained. These products can be separated and recovered by applying known techniques such as phase separation, extraction, distillation and adsorption.

In accordance with the present invention, the desired oxides can be produced continuously and at lower costs, since the microorganisms which have lost their methane monooxygenase activity can be reactivated or regenerated for repeated use in the production process. In addition, since the present method makes to reduce waste microorganisms and cuts down the cost of the disposal of waste liquid, it is possible to reduce the production costs of microorganisms and enzymes.

Therefore, the present invention is of significance in fields including chemical industries, pharmaceuticals, agricultural chemicals, waste water disposal and the like.

The present invention will now be explained with reference to the examples.

It is understood, however, that the cultivation of methane-utilizing bacteria was carried out by the following procedures.

Eight (8) l of a medium, shown in Table 1, were charged into a jar fermenter having a volume of 10 l, sterilized at 120° C. for 20 minutes and, thereafter, cooled. Added to this medium were 85 ml of a medium, shown in Table 2, which had been sterilized at 120° C. for 20 minutes.

TABLE 1

| | |
|---|---|
| Magnesium sulfate.7H$_2$O | 1.0 g |
| Potassium nitrate | 1.0 g |
| Calcium chloride | 50 mg |
| NaMoO$_4$ | 1 mg |
| FeSO$_4$.7H$_2$O | 500 μg |
| ZnSO$_4$.7H$_2$O | 400 μg |
| H$_3$BO$_4$ | 15 μg |
| CoCl$_2$.6H$_2$O | 50 μg |
| MnCl$_2$.4H$_2$O | 20 μg |
| NiCl$_2$.6H$_2$O | 10 μg |
| CuSO$_4$.5H$_2$O | 200 μg |
| EDTA | 250 μg |
| Distilled water | 1 l |

TABLE 2

| | |
|---|---|
| Na$_2$HOP$_4$.12H$_2$O | 43 g |
| KH$_2$PO$_4$ | 15.6 g |
| Fe-EDTA | 240 mg |
| Distilled water | 1 l |
| | (pH 6.8) |

Next, 50 ml of the medium shown in Table 1 were put in each of eight (8) Mayer's flasks having a volume of 500 ml, and sterilized at 120° C. for 20 minutes. Added to each flask were 0.5 ml of the medium shown in Table 2, which had been sterilized at 120° C. for 20 minutes. That medium was inoculated with one platinum loop of methane-utilizing bacteria. After the addition of 50 ml of methane, the flask was closed with a rubber stopper for a 3 day-shaking culture at 30° to 45° C. After the culture, the culture solutions were sterily transferred as the seed culture from the eitht flasks into the aforesaid jar fermenter, wherein culture was carried out for 3 days, while supplying thereto a mixed methane/air gas (methane air = 1:4) in a rate of 4 l per minute. After the concentration of the microbial cells had reached 1.5 mg/ml, a medium obtained by adding CuSO$_4$.5H$_2$O in a proportion of 1 mg/l to a medium prepared by mixing together the media of Tables 1 and 2 in a proportion of 100:1.5 was supplied to the jar fermenter in a rate of 1.6 l/hour for continuous culture, while passing through a sterile filter.

EXAMPLES 1 TO 5 AND COMPARATIVE EXAMPLE 1

Two (2) l of a culture solution of *Methylococcus capsulatus* NCIB 11132 continuously cultured according to the culture method of methane-utilizing bacteria were centrifuged to collect microorganisms.

The collected microorganisms were suspended in a reactivation solution, shown in Table 3, at a regulated microbial cells concentration of 3 mg/ml. Four hundreds (400) ml of this suspension were charged into a jar fermenter of 1 liter in volume, the temperature of which was then increased to 45° C. While passing air through the jar fermenter at a rate 200 ml per minute, methanol was added to the suspension at once at a regulated concentration of 10 mM. In addition, acetylene that was a killer substrate for the methane oxidation enzymes of methane-utilizing bacteria was supplied for 1 minute at a rate of 2 ml per minute to deactivate the methane oxidizability thereof. Ten minutes later, the activity of the microorganism in the reaction solution was measured Afterwards, while supplying air at a rate of 200 ml per minute, methanol was supplied under agitation at 900 r.p.m. to that solution at the rates shown in Table 4. Two hundreds and forty (240) minutes later, the activity of the microorganisms in the jar fermenter was measured. During reactivation, the culture solution was maintained at pH 7 with 1M nitric acid and 1M caustic potash. The results are set forth in Table 4.

TABLE 3

| (Reactivation Solution) | |
|---|---|
| Magnesium sulfate.7H$_2$O | 1.0 g |
| Potassium nitrate | 1.0 g |
| Calcium chloride | 100 mg |
| NaMoO$_4$ | 1 mg |
| FeSO$_4$.7H$_2$O | 500 μg |
| ZnSO$_4$.7H$_2$O | 400 μg |
| H$_3$BO$_4$ | 15 μg |
| CoCl$_2$.6H$_2$O | 50 μg |
| MnCl$_2$.4H$_2$O | 20 μg |
| NiCl$_2$.6H$_2$O | 10 μg |
| CuSO$_4$.5H$_2$O | 1500 μg |
| EDTA | 250 μg |
| Na$_2$HPO$_4$.12H$_2$O | 645 mg |
| KH$_2$PO$_4$ | 234 mg |
| Fe-EDTA | 3.6 mg |
| Distilled water | 1 l |
| (pH 6.8) | |

TABLE 4

| | Methanol Feeding Rate (nmol/min.·mg of microorganism) | Activity of Microorganism (nmol/min.·mg of microorganism) | | |
|---|---|---|---|---|
| | | I | II | III |
| Ex. 1 | 30 | 401 | 7 | 286 |
| Ex. 2 | 50 | 389 | 4 | 342 |
| Ex. 3 | 80 | 401 | 6 | 408 |
| Ex. 4 | 200 | 378 | 4 | 380 |
| Ex. 5 | 400 | 393 | 6 | 378 |
| Comp. Ex. 1 | 0 | 387 | 7 | 32 |

I: before acetylene addition
II: 10 minutes after acetylene addition
III: 240 minutes after methanol feeding As clearly understood from Table 4, satisfactory results are obtained, when methanol is supplied at a rate of 10 nmol/min.·mg of microorganism or higher, while any appreciable effect is not obtained, when methanol is supplied at a rate of higher than 400 nmol/min.·mg of microorganism, which brings about an increase in the production cost.

Incidentally, the activity of microorganism was measured by the following procedures The microbial cells were suspended in 5 mM of a PIPS buffer at a regulated concentration of 0.5 mg/ml, and 1 ml of the suspension was put in a Mayer's flask of 7 ml in volume, to which 2 ml of propylene were added. After the flask had been closed with a rubber plug, culture was carried out at 45° C. for 30 seconds. Then, methanol was added at a regulated concentration of 1 mM for further 3 minute-culture. Afterwards, the amount of propylene oxide produced was determined by chromatography, and was expressed in terms of the amount of propylene oxide produced per mg of microbial cells per minute.

EXAMPLES 6 TO 9 AND COMPARATIVE EXAMPLE 2

Culture was carried out in a manner analogous to that described in Example 1, except that *Methylococcus capsulatus* NCIB 11132 continuously cultured according to the culture method of methane-utilizing bacteria was applied at a regulated biocell concentration of 0.5 mg/ml. Afterwards, the methane oxidation activity of the microorganism was deactivated with acetylene. Ten minutes later, 10 ml of the culture solution were transferred from the jar fermenter into a Mayer's flask of 100 ml in volume, to which methanol was added at the concentrations specified in Table 5. That flask was closed with a cotton plug, and shaken at 45° C. and 200 r.p.m. Two hundreds and forty (240) minutes later, the activity of the microorganism was measured. The results are set forth in Table 5. That activity was 346 nmol/min..mg of microorganism and 0 nmol/min..mg of microorganism before and 10 minutes after the addition of actylene, respectively,

TABLE 5

| | Concentration of Methanol (mM) | Activity of Microorganism in 240 min. After Acetylene Addition (nmol/min.·mg of microorganism) |
|---|---|---|
| Ex. 6 | 6 | 230 |
| Ex. 7 | 12 | 344 |
| Ex. 8 | 18 | 367 |
| Ex. 9 | 24 | 382 |
| Comp. Ex. 2 | 0 | 28 |

EXAMPLES 10 TO 15 AND COMPARATIVE EXAMPLE 3

Example 1 was repeated, except that acetylene was supplied at a rate of 0.5 ml/min. for 1 minutes and, ten minutes later, a mixed gas of methane and air was supplied at a rate of 200 ml/min. in place of methanol. The results are set forth in Table 6.

TABLE 6

| | Methane/ Air Ratio (%) of Mixed Methane/ Air Gas | | Activity of Microorganism (nmol/min. · mg of microorganism) | | |
|---|---|---|---|---|---|
| | | | I | II | III |
| Ex. 10 | 3 | 97 | 431 | 24 | 474 |
| 11 | 6 | 94 | 428 | 17 | 472 |
| 12 | 77 | 23 | 451 | 26 | 478 |
| 13 | 83 | 17 | 444 | 27 | 460 |
| 14 | 91 | 9 | 444 | 25 | 294 |
| 15 | 97 | 3 | 456 | 23 | 182 |
| Comp. | 100 | 0 | 429 | 24 | 21 |

TABLE 6-continued

| Methane/ Air Ratio (%) of Mixed Methane/ Air Gas | Activity of Microorganism (nmol/min. · mg of microorganism) | | |
|---|---|---|---|
| | I | II | III |
| Ex. 3 | | | |

I: before acetylene addition
II: 10 minutes after acetylene addition
III: 240 minutes after the feed of mixed gas of methane and air Any special limitation is not imposed upon the ratio of methane to air. As clearly understood from Table 6, however, the reactivation of methane-utilizing bacteria is retarded in a state extremely short of oxygen, and does not occur at all in the absence of oxygen.

EXAMPLES 16 TO 20

Example 1 was repeated, except that formaldehyde was supplied in place of methanol at the rates specified in Table 7, and 140 minutes later, the activity of the microorganism was measured. The results are set forth in Table 7.

TABLE 7

| | Formaldehyde Feed Rate (nmol/min.·mg of microorganism) | Activity of Microorganism (nmol/min..mg of microorganism) | | |
|---|---|---|---|---|
| | | I | II | III |
| Ex. 16 | 30 | 376 | 4 | 173 |
| Ex. 17 | 50 | 398 | 0 | 205 |
| Ex. 18 | 100 | 398 | 8 | 210 |
| Ex. 19 | 200 | 378 | 0 | 180 |
| Ex. 20 | 400 | 392 | 7 | 136 |

I: before acetylene addition
II: 10 minutes after acetylene addition
III: 240 minutes after formaldehyde feed From Table 7, it is clear that difficulty is encountered in the reactivation of the methane-utilizing bacteria due to the toxicity of formaldehyde, when formaldehyde is supplied at a rate of 400 nmol/min..mg of microorganism or higher.

COMPARATIVE EXAMPLE 4

Example 18 was repeated, except that potassium formate was supplied at a rate of 100 nmol/min..mg of microbial cells in place of formaldehyde. As a result, the activity of the microbial cells was 387 nmol/min..mg of microbial cells before the addition of acetylene, 8 nmol/min..mg of microbial cells 10 minutes after the addition of acetylene and 24 nmol/min..mg of microbial cells 140 minutes after the supply of potassium formate.

EXAMPLES 21 TO 24

Example 3 was repeated, except that the nitrogen source shown in Table 8 was substituted for potassium nitrate in the reactivation solution shown in Table 3, and the adjustment of pH during reactivation was performed with 1M hydrochloric acid and 1M caustic potash. The results are set forth in Table 8.

TABLE 8

| | Nitrogen Source (mg/l) | Activity of Microorganism (nmol/min.·mg of microorganism) | | |
|---|---|---|---|---|
| | | I | II | III |
| Ex. 21 | Ammonium Sulfate 570 | 372 | 7 | 286 |
| Ex. 22 | Peptone 500 | 366 | 9 | 342 |
| Ex. 23 | L-glutamine 200 | 367 | 7 | 378 |

TABLE 8-continued

| | Nitrogen Source (mg/l) | Activity of Microorganism (nmol/min.·mg of microorganism) | | |
|---|---|---|---|---|
| | | I | II | III |
| Ex. 24 | L-asparagine 200 | 378 | 8 | 354 |

I: before addition of acetylene
II: 10 minutes after addition of acetylene
III: 240 minutes after methanol feed

COMPARATIVE EXAMPLE 5

Example 3 was repeated, except that potassium chloride was substituted for potassium nitrate in the reactivation solution shown in Table 3, and the adjustment of pH during reactivation was performed with potassium hydroxide. The activity of the microorganis was 372 nmol/min..mg of microorganism before the addition of acetylene, 9 nmol/min..mg of microorganism 10 minutes after the addition of acetylene and 24 nmol/min.mg of microorganism 240 minutes after the feeding of methanol.

EXAMPLES 25 TO 28 AND COMPARATIVE EXAMPLE 6

A culture solution of *Methylococcus capsulatus* NCIB 11132 cultured according to the culture method of methane-utilizing bacteria was centrifuged and washed three times with a reactivation solution shown in Table 9, which contained the salts shown in Table 10. Thereafter, the microbial cells were suspended in the same reactivation solution at a regulated microbial cells concentration of 3 mg/ml.

TABLE 9

| (Reactivation Solution) | |
|---|---|
| Potassium nitrate | 1.0 g |
| Calcium chloride | 100 mg |
| Magnesium chloride | 200 mg |
| $Na_2HPO_4.12H_2O$ | 645 mg |
| $KH_2PO_4$ | 234 mg |
| Distilled water | 1 l |
| | (pH 6.8) |

Four hundreds (400) ml of this suspension were charged into a jar fermenter of 400 ml in volume, the temperature of which was then increased to 45° C. After propylene oxide had been added to the suspension in a proportion of 2 nmol/400 ml, air and methanol were supplied thereto in the respective proportions of 80 ml/min. and 300 nmol/min..mg of microbial cells for 30 minutes. Thirty (30) minutes later, the microbial cells were centrifuged out for the removal of the remaining propylene oxide, and were again suspended in the same reactivation solution. Fifty (50) minutes later, methanol and air were supplied to the suspension in the respective proportions of 80 nmol/min.mg of microorganism and 40 ml/min, and the sulfur compounds shown in Table 10 were added thereto. The suspension was stirred for further 240 minutes. The results are set forth in Table 10.

TABLE 10

| | Sulfur Source (mg/l) | Activity of Microorganism (nmol/min.·mg of microorganism) | | |
|---|---|---|---|---|
| | | I | II | III |
| Ex. 25 | Sodium sulfate 50 | 403 | 24 | 376 |
| Ex. 26 | Sodium sulfide 50 | 387 | 32 | 362 |
| Ex. 27 | Hydrosulfide 50 | 387 | 36 | 343 |

TABLE 10-continued

| | Sulfur Source (mg/l) | Activity of Microorganism (nmol/min.·mg of microorganism) | | |
|---|---|---|---|---|
| | | I | II | III |
| Ex. 28 | Sodium sulfhydrate 50 | 392 | 18 | 346 |
| Comp. Ex. 6 | Not added | 380 | 32 | 24 |

I: before addition of propylene oxide
II: 30 minutes after addition of propylene oxide
III: 240 minutes after feeding of methanol and sulfur

EXAMPLE 29

A culture solution of *Methylococcus capsulatus* NCIB 11132 continuously cultured according to the culture method of methane-utilizing bacteria was diluted with the reactivation solution shown in Table 3 to a regulated microorganism concentration of 3 mg/ml. Four hundreds (400) ml of the thus diluted solution were charged in a jar fermenter of 1 l in volume, the temperature of which was then increased to 45° C. That solution was stirred at 900 r.p.m., while passing propylene and air at the respective rates of 150 ml and 50 ml per minute. Simultaneously with the supply of propylene, methanol was supplied in a proportion of 300 nmol/mg of microorganism per minute. Ninety (90) minutes later, the feed of propylene and methanol was interrupted, and propylene oxide accumulated in the reaction solution was expelled by the supply of air at a rate of 3.2 l per minute. Twenty (20) minutes later, the supply of air was interrupted, and a mixed gas of methane and air (methane:air=4:1) was supplied at a rate of 200 ml per minute. Two hundreds and forty (240) minutes later, the activity of the microorganism in the jar fermenter was measured. It is to be noted that during reactivation, the microorganism did not propagate. The results are set forth in Table 11.

TABLE 11

| Amount of Propylene Oxide in Water in 90 minutes After Propylene Feeding | Activity of Microorganism (nmol/min.·mg of microorganism) | | |
|---|---|---|---|
| | I | II | III |
| 2.6 | 380 | 178 | 355 |

I: before addition of propylene
II: 90 minutes after addition of propylene
III: 240 minutes after feeding of mixed gas of methane and air

EXAMPLE 30

A culture solution of *Methylococcus capsulatus* NCIB 11132 continuously cultured according to the culture method of methane-utilizing bacteria was diluted with the reactivation solution shown in Table 3 to a regulated microbial cells concentration of 3 mg/ml. Four hundreds (400) ml of the thus diluted solution were charged in a jar fermenter of 1 l in volume, the temperature of which was then increased to 37.5° C. That solution was stirred at 900 r.p.m., while passing 1-butene and air at the respective rates of 320 ml and 80 ml per minute. Simultaneously with the supply of 1-butene, methanol was supplied in a proportion of 300 nmol/mg of microbial cells per minute. After 150 minutes, the supply of 1-butene and methanol was interrupted. The reaction solution was centrifuged for the removal of 1,2-butylene oxide, and was again suspended in 400 ml of a fresh reactivation solution shown in Table 3. In the meantime, the time required for centrifugation and resuspension was 20 minutes. Then, the resulting solution was maintained at 37.5° C., while supplying thereto air and methane in the respective rates of 40 ml and 160 ml. After 400 minutes, the activity of the microorganism in the jar fermenter was measured. It is to be noted that during reactivation, the microorganism did not propagate. The results are set forth in Table 12.

TABLE 12

| Amount of Butylene Oxide in Water in 150 min. After 1-Butene Supply (mM) | Activity of Microorganism (nmol/min.·mg of microorganism) | | |
|---|---|---|---|
| | I | II | III |
| 6.2 | 332 | 106 | 354 |

I: before addition of 1-butene
II: 150 minutes after addition of 1-butene
III: 400 minutes after feeding of air and methane

EXAMPLES 31 AND 34

Four (4) Mayer's flasks of 500 ml in volume, each containing 50 ml of a medium prepared by the method of Whittenbury et al (J. Gen. Microbiol., 61, pp. 205–208, 1970), were provided and sterilized under pressure at 120° C. for minutes. After cooling, the gaseous phases were replaced with a mixed gas of methane and air having a methane/air ratio of 1:4. Then, the cells of *Methylomonas agile* NCIB 11124, *Methylocystis parvus* NCIB 587 11129, *Methylosinus trichosporium* NCIB 11131 and *Methylobacter capsulata* NCIB 11128 were inoculated into the media for shaking culture at 30° C. for 32 hours.

After the completion of the culture, the culture solutions were centrifuged to collect the microorganism, which were in turn suspended in the reactivation solution specified in Table 13 at a regulated microorganism concentration of 1 mg/ml. Ten (10) ml of this suspension were put in a Mayer's flask of 250 ml in volume, which was closed with a rubber stopper after addition of 2 mM of methanol and 100 μl acetylene. After shaking culture had been carried out at 30° C. for 10 minutes, the rubber stopper was pulled out of the flask to pass air therethrough at a rate of 1 ( per minute for 10 minutes, thereby removing the remaining acetylene. One hundred (100) ml of methane were added to the flask, which was then closed with the rubber stopper for shaking at 30° C. for 220 minutes. Thereafter, the activity of the microorganism was measured. The results are set forth in Table 14.

TABLE 13

| (Reactivation Solution) | |
|---|---|
| Magnesium sulfate.7H$_2$O | 1.0 g |
| Potassium nitrate | 1.0 g |
| Calcium chloride | 100 mg |
| Na$_2$HPO$_4$.12H$_2$O | 645 mg |
| KH$_2$PO$_4$ | 234 mg |
| Distilled water | 1 l |

TABLE 14

| | Bacteria | Activity of Microorganism (nmol/min.·mg of microorganism) | | |
|---|---|---|---|---|
| | | I | II | III |
| Ex. 31 | *Methylomonas agile* NCIB 11124 | 82 | 0 | 64 |
| Ex. 32 | *Methylocystis parvus* NCIB 11129 | 44 | 0 | 32 |
| Ex. 33 | *Methylosinus trichosproium* NCIB 11131 | 92 | 0 | 78 |
| Ex. 34 | *Methylobacter capslata* | 72 | 0 | 81 |

TABLE 14-continued

| Bacteria | Activity of Microorganism (nmol/min.·mg of microorganism) | | |
|---|---|---|---|
| | I | II | III |
| NCIB 11128 | | | |

I: before acetylene addition
II: 10 minutes after acetylene addition
III: 240 minutes after air feeding

EXAMPLES 35 TO 41

Four hundreds (400) ml of each culture solution of *Methylomonas methanica* NCIB 11130, *Methylomonas agile* NCIB NCIB 11124, *Methylomonas albus* NCIB 1112, *Methylosinus trichosporium* NCIB 11131, *Methylosinus sporium* NCIB 11126, *Methylocystis parvus* NCIB 11129 and *Methylobacter capsulata* NCIB 11128 were centrifuged to collect microbial cells. The collected microbial cells were suspended in the reactivation solution shown in Table 15 at a regulated microbial cells concentration of 0.5 mg/ml. Four hundreds (400) ml of this suspension were charged in a jar fermenter of 1 l in volume, the temperature of which was increased to 31° C. Then, that suspension was stirred at 900 r.p.m., while passing propylene and air through the jar fermenter at the respective rates of 150 ml and 150 ml per minute. Simultaneously with the supply of propylene, methanol was supplied in a rate of 300 nmol/mg of microbial cells per minute. Thirty (30) minutes later, the supply of propylene and methanol was interrupted, and air was supplied at a rate of 5 l per minute to expel propylene oxide accumulated in the reaction solution. Twenty (20) minutes later, the amount of air supplied was decreased to 25 ml, and methane was supplied in a further rate of 110 ml/min. One hundred and eighty (180) minutes and 300 minutes after the supply of a mixed methane/air gas, the activity of the microorganism in the jar fermenter was measured. The results are set forth in Table 15.

TABLE 15

| (Reactivation Solution) | |
|---|---|
| Magnesium sulfate.7H$_2$O | 1.0 g |

TABLE 15-continued

| (Reactivation Solution) | |
|---|---|
| Potassium nitrate | 1.0 g |
| Calcium chloride | 50 mg |
| NaMoO$_4$ | 1 mg |
| FeSO$_4$.7H$_2$O | 500 μg |
| ZnSO$_4$.7H$_2$O | 400 μg |
| H$_3$BO$_4$ | 15 μg |
| CoCl$_2$.6H$_2$O | 50 μg |
| MnCl$_2$.4H$_2$O | 20 μg |
| NiCl$_2$.6H$_2$O | 10 μg |
| CuSO$_4$.5H$_2$O | 500 μg |
| EDTA | 250 μg |
| Na$_2$HPOhd 4.12H$_2$O | 645 mg |
| KH$_2$PO$_4$ | 234 mg |
| Fe-EDTA | 3.6 mg |
| Distilled water | 1 l |
| | (pH 6.8) |

TABLE 16

| Example No. | Bacteria | Amount of Propylene Oxide in Water 30 min After Propylene Supply (mM) | Before Propylene Supply | 30 min. After Propylene Supply | After the Supply of Mixed Methane/ Air Gas | |
|---|---|---|---|---|---|---|
| | | | | | 180 min. | 300 min. |
| 35 | *Methylomonas methanica* NCIB 11130 | 1.9 | 472 | 108 | 247 | 338 |
| 36 | *Methylomonas agile* NCIB 11124 | 1.7 | 402 | 83 | 104 | 152 |
| 37 | *Methylomonas albus* NCIB 11123 | 1.9 | 382 | 79 | 205 | 314 |
| 38 | *Methylosinus trichosporium* NCIB 11131 | 2.7 | 372 | 116 | 398 | 409 |
| 39 | *Methylosinum sporium* NCIB 11126 | 1.8 | 402 | 148 | 332 | 401 |
| 40 | *Methylocystis parvus* NCIB 11129 | 2.3 | 490 | 112 | 410 | 506 |
| 41 | *Methylobacter capsulata* NCIB 11128 | 1.4 | 332 | 134 | 259 | 346 |

EXAMPLES 42 TO 47 AND COMPARATIVE EXAMPLE 7

The reactivation solution specified in Table 15 was added to a culture solution of *Methylococcus capsulatus* NCIB 11132 continuously cultured at 45° C. according to the culture method of methane-utilizing bacteria in such a manner that the microorganism concentration was on the order of 0.3 mg/l and 500 ml of the resulting solution was then charged in a jar fermenter of 1 l in volume, the temperature of which was in turn increased to 45° C. Thereafter, while passing 110 ml/min of methane and 50 ml/min. of air through that fermenter, 1 ml of acetylene was added thereto at once to deactivate the methane oxidizability of the microorganism.

Ten (10) minutes later, the microorganisms were centrifuged and washed three times with the reactivation solution specified in Table 17. Thereafter, the microorganisms were suspended in the same reactivation solution at a regulated microorganism concentration of 1.45 mg/ml. Afterwards, 10 ml portions of the suspension were put in Mayer's flasks of 250 ml in volume.

Then, varied concentrations of potassium nitrate were added into such flasks, followed by closing with stoppers. Thereafter, 50 ml portions of methane were added into the flasks for 80 r.p.m. shaking culture at 45° C.

Three (3) hours later, the activity of the microorganism was measured. The results are set forth in Table 18.

TABLE 17

| | |
|---|---|
| Magnesium sulfate.7H$_2$O | 1 g |
| Magnesium chloride.6H$_2$O | 203 mg |
| Calcium chloride | 50 mg |
| NaMoO$_4$ | 1 mg |
| FeCl$_3$.6H$_2$O | 500 μg |
| ZnCl$_2$ | 200 μg |
| H$_3$BO$_4$ | 15 μg |
| CoCl$_2$.6H$_2$O | 50 μg |
| MnCl$_2$.4H$_2$O | 20 μg |
| NiCl$_2$.6H$_2$O | 10 μg |
| CuCl$_2$.2H$_2$O | 340 μg |
| EDTA | 250 μg |
| Na$_2$HPO$_4$.12H$_2$O | 645 mg |
| KH$_2$PO$_4$ | 234 mg |
| Fe-EDTA | 3.6 mg |
| Distilled water | 1 l |

TABLE 18

| | Amount of Potassium Nitrate Added (g/l) | Activity of Microorganism (nmol/min. · mg microorganism) | |
|---|---|---|---|
| | | I | II |
| Ex. | | | |
| 42 | 0.026 | 0 | 105 |
| 43 | 0.065 | 0 | 133 |
| 44 | 0.13 | 0 | 180 |
| 45 | 0.26 | 0 | 307 |
| 46 | 0.79 | 0 | 401 |
| 47 | 2.63 | 0 | 337 |
| Comp. Ex. | | | |
| 7 | 0 | 0 | 85 |

I: 10 min. after addition of acetylene
II: 180 min. after addition of air and methane It is noted that the activity of the microorganism was 578 nmol/min..mg of microorganism before the addition of acetylene.

EXAMPLES 48 TO 53 AND COMPARATIVE EXAMPLE 8

Experiments were conducted in a manner similar to that described in Examples 42 to 47, except that 1 g/l of potassium nitrate was added in place of magnesium sulfate. 7H$_2$O shown in Table 17, and vaired concentrations of magnesium sulfate.7H$_2$O were added in lieu of potassium nitrate shown in Table 18. The results are set forth in Table 19.

TABLE 19

| | Amount of Magnesium Sulfate.7H$_2$O Added (g/l) | Activity of Microorganism (nmol/min. · mg microorganism) | |
|---|---|---|---|
| | | I | II |
| Ex. | | | |
| 48 | 0.013 | 0 | 229 |
| 49 | 0.063 | 0 | 257 |
| 50 | 0.013 | 0 | 362 |
| 51 | 0.032 | 0 | 402 |
| 52 | 0.064 | 0 | 424 |
| 53 | 0.32 | 0 | 295 |
| Comp. Ex. | | | |
| 8 | 0 | 0 | 183 |

I: 10 minutes after addition of acetylene
II: 180 minutes after the feed of air and methane

EXAMPLES 54 TO 59 AND COMPARATIVE EXAMPLE 9

In the culture method of methane assimilable bacteria, the concentration of magnesium sulfate.7H$_2$O in a medium was adjusted to 7 g/l. *Methylocystis parvus* NCIB 11129 was cultured at 31° C.

Five hundreds (500) ml of a microbial culture solution (having a microorganism concentration of 0.49 mg/ml) were placed in an 1 liter-jar fermenter, the temperature of which was then increased to 33° C. Thereafter, while supplying 150 ml/min. of propylene and 150 ml/min. of air to the jar fermenter, that solution was stirred at 900 r.p.m. Simultaneously with the supply of propylene, methanol was supplied at a rate of 300 nmol/mg of microorganism per minute. Thirty (30) minutes later, the supply of propylene and methanol was interrupted, and air was supplied at a rate of 5 l per minute to expel propylene oxide accumulated in the reaction solution. Subsequently, the microorganisms were centrifuged and washed four times with the reactivation solution shown in Table 17, from which magnesium sulfate.7H$_2$O had been removed. Thereafter, the microorganisms were suspended in the same solution at a microorganism concentration regulated to 0.5 mg/ml, and 20 ml portions of the suspension were placed in Mayer's flasks of 250 ml in volume. Varied concentrations of magnesium sulfate.7H$_2$O were added into the flasks, followed by closing with rubber plugs. Thereafter, 50 ml of methane were added to the flasks, which were then shaken at 30° C. and 80 r.p.m.

Three hundreds (300) minutes after the initiation of shaking culture, the activity of the microorganisms was measured. The results are set forth in Table 20.

TABLE 20

| | Amount of Magnesium Sulfate 7H$_2$O Added (g/l) | Activity of Microorganism (nmol/min. · mg of microorganism) 300 min. After the Addition of Mixed Methane/Air Gas |
|---|---|---|
| Ex. | | |
| 54 | 1.0 | 432 |
| 55 | 3.5 | 428 |
| 56 | 7.0 | 403 |
| 57 | 16.0 | 461 |
| 58 | 30.0 | 326 |
| 59 | 40.0 | 282 |
| Comp. Ex. | | |
| 9 | 0 | 68 |

It is noted that propylene oxide in water was 2.2 mM at 30 minutes after the supply of propylene, the activity of the microorganism before the supply of propylene was 449 nmol/min..mg of microorganism and the activity of the microorganism after centrifugation and washing was 142 nmol/min..mg of microorganism.

EXAMPLES 60–63 AND COMPARATIVE EXAMPLE 10

Two (2) l of a culture solution of *Methylococcus capsulatus* NCIB 11132 continuously cultured according to the culture method of methane-utilizing bacteria were centrifuged to collect microbial cells, which were thereafter suspended in 200 ml of a 4-mM phosphate buffer (pH 6.8), and the resulting suspension was again centrifuged to wash the microbial cells. Such washing was repeated further twice. Afterwards, the microbial cells were suspended in a 4-mM phosphate buffer (pH 6.8) at a bacterial concentration of 2 mg/ml, and 400 ml of the resulting suspension were put in a jar fermenter of 1 l in volume, which was in turn elevated to a temperature of 45° C. Then, while air was supplied to the jar fermenter at a rate of 40 ml per minutes, potassium formate was added thereto at a concentration of 10 mM. Further, acetylene that was a killer substrate for methane monooxygenase was supplied to the jar fermenter at a rate of 1 ml per minute for 1 minute to deactivate the methane oxidizability. After 10 minutes, L-methionic acid was added to the jar fermenter at the rates specified in Table 21, and the activity of the microbial cells therein was determined after 240 minutes. It is noted that during the regeneration of the microbial cells, the microbial cells solution was maintained at pH 7.0 with formic acid. The results are set out in Table 21.

TABLE 21

|  | Amount of L-Methionine (mg/l) | Activity of Microbial Cells (nmol/min. · mg of cells) | | |
| --- | --- | --- | --- | --- |
|  |  | Before Acetylene Addition | 10 min. After Acetylene Addition | 240 min. After L-methionine Addition |
| Ex. |  |  |  |  |
| 60 | 10 | 316 | 0 | 182 |
| 61 | 25 | 298 | 0 | 206 |
| 62 | 50 | 308 | 0 | 212 |
| 63 | 100 | 288 | 0 | 176 |
| Comp. Ex. |  |  |  |  |
| 10 | 0 | 298 | 0 | 7 |

EXAMPLE 64 AND COMPARATIVE EXAMPLE 11

*Methylococcus capsulatus* NCIB 11132 cultured according to the culture method of methane-utilizing bacteria was collected, suspended and cultured in a similar manner as described in Example 60, and propylene oxide in place of acetylene was added all at once at a concentration of 4 mM to deactivate the methane oxidizability. After 30 minutes, air was supplied at a rate of 3.2 l per minute for 10 minutes to remove propylene oxide, and 50 mg/l of L-methionine were added, while supplying air at a rate of 40 m/min. After 240 minutes, the activity of microbial cells was measured. It is noted that Comparative Example 11 was carried out in a similar manner as in Example 64, but in the absence of L-methionine. The results are set out in Table 22.

EXAMPLES 65 TO 70 AND COMPARATIVE EXAMPLES 12 TO 14

Two hundreds (200) ml of a culture solution of *Methylococcus capsulatus* NCIB 11132 continuously cultured according to the culture method of methane-utilizing bacteria were centrifuged to collect microorganisms, which were then suspended in the regeneration solution specified in Table 23 at a regulated microbial cell concentration of 1 mg/ml.

Four hundreds (400) ml of this suspension were charged into a jar fermenter of 1 liter in volume, the temperature of which was in turn increased to 45° C., while supplying air thereto at a rate of 100 ml per minute. Subsequently, sodium benzoate was added to that fermenter in the amount specified in Table 24, followed by 10 minute-stirring. Afterwards, propylene and methanol were supplied to that fermenter for 30 minutes at the respective rates of 320 ml/min. and 350 nmol/min..mg of microorganism to produce propylene oxide.

After 30 minutes, the supply of propylene and methanol was interrupted, and air was supplied at a rate of 3.2 liters per minute to expel the remaining propylene oxide out of the reaction solution. After 15 minutes, the rate of the air supplied was decreased to 35 ml/min. After the temperature had been identified to be 45° C., the regeneration of the microorganism was initiated by the supply of methane at a rate of 120 ml/min. Thereafter, the activity of the microorganism was measured in succession to determine the time by which the regeneration of the microorganism occurred. The results are set forth in Table 24.

TABLE 23

| (Regeneration Solution) | |
| --- | --- |
| Magnesium sulfate.7H$_2$O | 1.0 g |
| Potassium nitrate | 1.0 g |
| Calcium chloride | 100 mg |
| NaMoO$_4$ | 1 mg |
| FeSO$_4$.7H$_2$O | 500 μg |
| ZnSO$_4$.7H$_2$O | 400 μg |
| H$_3$BO$_4$ | 15 μg |
| CoCl$_2$.6H$_2$O | 50 μg |
| MnCl$_2$.4H$_2$O | 20 μg |
| NiCl$_2$.6H$_2$O | 10 μg |
| CuSO$_4$.5H$_2$O | 500 μg |
| EDTA | 250 μg |
| Na$_2$HPO$_4$.12H$_2$O | 645 mg |
| KH$_2$PO$_4$ | 234 mg |
| Fe-EDTA | 3.6 mg |
| Distilled water | 1 liter |
|  | (pH 6.8) |

TABLE 22

|  | Amount of L-Methionine (mg/l) | Activity of Microbial Cells (nmol/min. · mg of cells) | | |
| --- | --- | --- | --- | --- |
|  |  | Before Propylene Oxide Addition | 10 min. After Propylene Oxide Addition | 240 min. After L-methionine Addition |
| Ex. |  |  |  |  |
| 64 | 50 | 274 | 26 | 202 |
| Comp. Ex. |  |  |  |  |
| 11 | 0 | 280 | 31 | 16 |

TABLE 24

| Example | Amount of Sodium Benzoate Added (mM) | Microbial Activity at the Time of Initiation of Reaction (nmol/min. · mg microorganism) | Microbial Activity at the Time of Regeneration (nmol/min. · mg microorganism) | Time until Initiation of Regeneration (min.) |
|---|---|---|---|---|
| 65 | 0.25 | 390 | 67 | 105 |
| 66 | 0.88 | 386 | 64 | 95 |
| 67 | 1.75 | 388 | 54 | 85 |
| 68 | 2.50 | 380 | 58 | 50 |
| 69 | 3.75 | 386 | 62 | 120 |
| 70 | 5.0 | 490 | 56 | 115 |
| Comparative Example | | | | |
| 12 | 10.0 | 487 | 58 | 175 |
| 13 | 20.0 | 398 | 60 | 190 |
| 14 | 0 | 496 | 57 | 180 |

It is noted that the activity of microorganisms were measured in the following manner. The microorganisms were suspended in a 5 mM PIPES buffer at a regulated concentration of 0.5 mg/ml, and 1 ml of the suspension was put in a Mayer's flask of 7 ml in volume. The flask was closed with a rubber stopper, followed by the addition of 2 ml of propylene, and was then shaken with a rate of 300 r.p.m. at 45° C. for 30 seconds to agitate the content. Subsequently, methanol was added to the flask at a regulated concentration of 1 mM, which was cultured under shaking for 3 minutes. Afterwards, gas chromatography was applied to determine the amount of the propylene oxide produced per minute per 1 mg of microorganism.

EXAMPLES 71 TO 74 AND COMPARATIVE EXAMPLES 15, 16

Operations similar to those described in Example 65 were carried out, except that 1-butene was substituted for propylene, and air was supplied at a rate of 4 liters per minute for the removal of butylene oxide after the termination of the reaction. The results are set forth in Table 25.

TABLE 25

| Example | Amount of Sodium Benzoate Added (mM) | Microbial Activity at the Time of Initiation of Reaction (nmol/min. · mg microorganism) | Microbial Activity at the Time of Regeneration (nmol/min. · mg microorganism) | Time until Initiation of Regeneration (min.) |
|---|---|---|---|---|
| 71 | 0.25 | 372 | 92 | 40 |
| 72 | 0.88 | 381 | 88 | <30 |
| 73 | 2.50 | 378 | 83 | <30 |
| 74 | 5.0 | 372 | 85 | 60 |
| Comparative Example | | | | |
| 15 | 10.0 | 381 | 81 | 125 |
| 16 | 0 | 382 | 93 | 120 |

EXAMPLES 75 TO 77 AND COMPARATIVE EXAMPLES 17, 18

Operations similar to those described in Example 65 were carried out, except that benzoic acid was used in place of sodium benzoate, and adjusted pH to 7.0 with 0.5M potassium hydroxide. The results are shown in Table 26.

TABLE 26

| Example | Amount of Benzoic Acid Added (mM) | Microbial Activity at the Time of Initiation of Reaction (nmol/min. · mg microorganism) | Microbial Activity at the Time of Regeneration (nmol/min. · mg microorganism) | Time until Initiation of Regeneration (min.) |
|---|---|---|---|---|
| 75 | 0.25 | 418 | 71 | 100 |
| 76 | 1.75 | 426 | 68 | 75 |
| 77 | 5.0 | 440 | 64 | 110 |
| Comparative Example | | | | |
| 17 | 0 | 389 | 58 | 185 |
| 18 | 10.0 | 443 | 59 | 180 |

EXAMPLE 78

This example was carried out with using the apparatus system shown in FIG. 1.

Two point four (2.4) liters of a medium obtained by mixing together the medium specified in Table 1 except that the concentration of CuSO$_4$.5H$_2$O was changed to 1000 μg and the medium specified in Table 2 in a mixing ratio of 100:1.5 were charged into a regenerating vessel B through a sterile filter.

On the other hand, 50 ml portions of a medium having the same composition, which had been treated through a sterile filter for the removal of infectious microbes, were charged into six Mayer's flasks of 500 ml in volume. One platinum loop of slant-cultured *Methylococcus capsulatus* NCIB 11132 was inoculated into each flask, which was then closed with a rubber plug, followed by pouring of 100 ml of methane. Culture was subsequently carried out at 45° C. for 3 days. The obtained culture solution amounting to 300 ml in all was inoculated on the medium contained in the vessel B described above. While supplying a mixed methane/air gas of 1:4 at a rate of 1.35 liters per minute to the regeneration vessel B maintained at 45° C., culture was carried out at 600 r.p.m. for 24 hours. In consequence, the microbial concentration reached to 1 mg/ml.

Next, the microbial suspension was supplied to a reactor vessel A at a rate of 20 ml per minute by means of a pump 1. At the same time, a pump 2 was started to feed the microbial suspension from the reactor A to the upper portion of a scrubber C at a rate of 60 ml per minute. It is here noted that the reactor and scrubber were maintained at 45° C. with hot water.

Simultaneously with air supply at a rate of 120 ml per minute, a 10 v/v % methanol solution was supplied under 900 r.p.m. agitation to the reactor vessel at a rate of 65 μl per minute. A pump 3 was started to guide the microbial suspension from the reactor vessel to the upper portion of a scrubber D at a rate of 20 ml per minute and return it to the regenerating vessel through its lower portion. All the amount of the mixed methane/air effluent gas was admitted into the lower portion of the scrubber D. A gas leaving the upper portion of the scrubber D is guided into the lower portion of the scrubber C, and was vented from the upper portion thereof. After the apparatus system had been operated for 24 hours in such a state, the overall microbial concentration in the reaction system reached 2.2 mg/ml.

A 10 v/v % methanol solution was supplied to the regenerating vessel at a rate of 100 μl/min. and, at the same time, the amount of the methanol supplied to the reactor vessel was decreased to 25 μl/min. Subsequently, propylene was fed from the lower portion of the reactor vessel at a rate of 320 ml/min to initiate the production of propylene oxide. More exactly, the microorganism-containing reaction mixture was supplied from the reactor vessel to the upper portion of the scrubber at a rate of 100 ml/min. to collect the produced propylene oxide and discharge it therefrom to the outside, while the microorganism-containing reaction mixture was guided to the regenerating vessel at a rate of 20 ml/min., where the microorganisms having decreased methane oxidizability were regenerated, as already mentioned, and were thereafter again returned to the reactor vessel for the production of propylene oxide.

After the initiation of the reaction, a fresh regenerating solution in which the concentration of copper sulfate specified in Table 1 was changed to 1500 μg per liter was supplied at a rate of 120 ml/hr. to make up for decreases in the amount of the solution due to the evaporation of moisture and promote the regeneration of microorganisms, and the reaction mixture containing surplus microorganisms was discharged from the system to the outside. It is noted that the regeneration vessel was controlled to pH 7 with 0.5 M nitric acid. The gas collected with the scrubbers was analyzed by gas chromatography to determine the quantity of the propylene oxide produced. The results are set forth in Table 27.

TABLE 27

| | Time (hour) Elapsed After Reaction Initiation | | | | | |
|---|---|---|---|---|---|---|
| | 0 | 1 | 24 | 168 | 240 | 288 |
| Microbial Concentration in Reactor (mg/ml) | 2.2 | 2.2 | 2.4 | 2.1 | 2.3 | 2.3 |
| Microbial Activity in Reactor (nmol/min. · mg of microorganism) | 338 | 284 | 178 | 182 | 191 | 176 |
| Microbial Activity in Regenerating Vessel (nmol/min. · mg of microorganism) | 338 | 311 | 220 | 236 | 242 | 230 |
| Amount of Propylene Oxide Produced (mmol/hr.) | — | 3.15 | 2.86 | 2.77 | 2.79 | 2.78 |
| Propylene Oxide Concentration in Regenerating Vessel (mM) | 0 | 0.08 | 0.06 | 0.06 | 0.07 | 0.06 |

As clearly understood from the table, propylene oxide could continuously be produced in a stable state by regenerating the microorganisms in the regenerating 246 vessel. It is noted that the activity of microorganisms was measured in the following manner. The microorganisms were suspended in a 5 mM PIPES buffer at a regulated concentration of 0.5 mg/ml, and 1 ml of the suspension was put in a Mayer's flask of 7 ml in volume. The flask was closed with a rubber stopper, followed by the addition of 2 ml of propylene, and was then vigorously shaken at 45° C. for 30 seconds. Subsequently, methanol was added to the flask at a regulated concentration of 1 mM, which was in turn vigorously shaken at 45° C for 3 minutes. Afterwards, gas chromatography was applied to determine the quantity of the propylene oxide produced per minute per 1 mg of microorganism.

COMPARATIVE EXAMPLE 19

Example 78 was repeated, except that no methanol was supplied to the regenerating vessel, and only air was fed at a rate of 1.35 liters per minute in place of the mixed methane/air gas. Where the regenerating vessel was not permitted to work, the production of propylene oxide substantially stopped after the lapse of 24 hours. The results are set forth in Table 28.

TABLE 28

| | Time (hour) Elapsed After Reaction Initiation | | | |
|---|---|---|---|---|
| | 0 | 1 | 7 | 24 |
| Microbial Concentration in Reactor (mg/ml) | 2.3 | 2.3 | 2.1 | 1.5 |
| Microbial Activity in Reactor (nmol/min. · mg of microorganism) | 352 | 161 | 36 | 9 |
| Microbial Activity in Regenerating Vessel (nmol/min. · mg of microorganism) | 358 | 183 | 42 | 9 |
| Amount of Propylene Oxide Produced (mmol/hr.) | — | 2.98 | 0.21 | <0.1 |
| Propylene Oxide Concentration in Regenerating Vessel (mM) | 0 | 0.06 | <0.01 | <0.01 |

EXAMPLE 79

Figure 2:
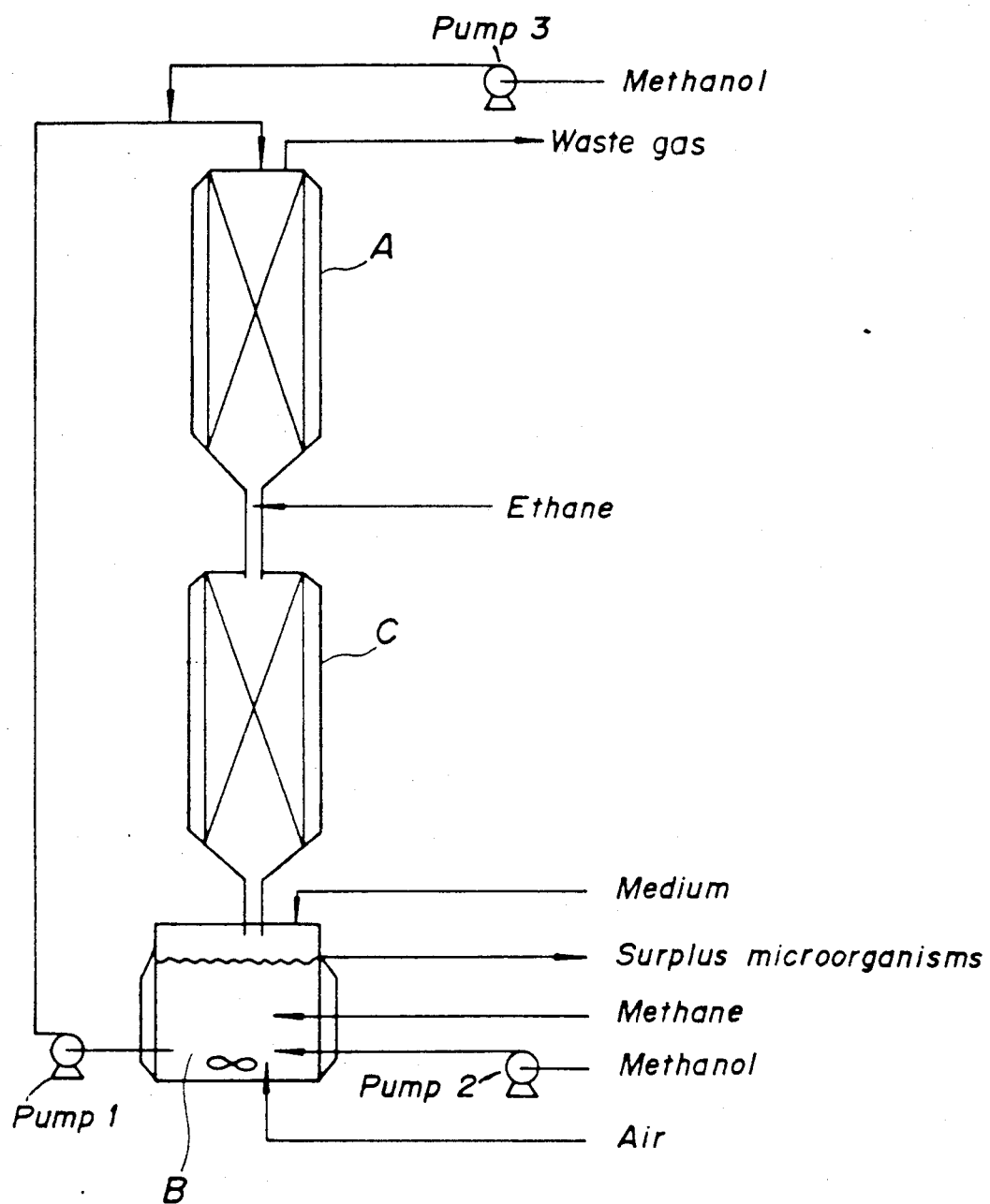

This example was carried out with using the apparatus system shown in FIG. 2.

Two point four (2.4) liters of a medium obtained by mixing together the medium specified in Table 1 except that the concentration of $CuSO_4.5H_2O$ was changed to 1000 μg and the medium specified in Table 2 in a mixing ratio of 100:1.5 were charged into a regenerating vessel B through a sterile filter, and were inoculated with a seed culture of *Methylococcus capsulatus* NCIB 11132 cultured in a manner similar to that described in Example 78. Air and methane were supplied under 900 r.p.m. agitation to the regenerating vessel at the respective rates of 1200 ml/min. and 230 ml/min. which was maintained at 45° C.

Next, a pump 1 was started to supply the microbial suspension to the upper end of a reactor vessel A at a rate of 10 ml/min. for circulation therethrough. After 24 hours, a pump 2 was actuated to start to supply a 10 v/v % methanol solution to the lower portion of the regenerating vessel at a rate of 200 μl/min. and, at the same time, the amount of methane supplied to the regenerating vessel was decreased from 230 μl/min. to 30 μl/min. After the lapse of further 24 hours, the microbial concentration reached 1.8 mg/min., whereupon the reaction begun to occur.

Ethane was supplied from the reactor vessel through its lower portion at a rate of 320 ml/min. and, at the same time, a pump 3 was actuated to supply an 1 v/v methanol solution from the upper portion of the reactor vessel at a rate of 40 μl/min. During the reaction, a fresh regenerating solution in which the concentration of copper sulfate specified in Table 1 was changed to 1500 μg/l was supplied at a rate of 120 ml/min. so as to keep constant the amount of the solution contained in the regenerating vessel, and an extra microbial suspension was discharged from within the system to the outside. During the reaction, pH was also adjusted to 7.2 with 0.5M nitric acid and potassium hydroxide. Moreover, acetaldehyde in the effluent gas collected from the upper portion of the reaction vessel was analyzed by gas chromatography. The results are set forth in Table 29.

TABLE 29

|  | Time (hour) Elapsed After Reaction Initiation | | | | |
|---|---|---|---|---|---|
|  | 0 | 1 | 24 | 48 | 72 |
| Microbial Concentration in Reactor (mg/ml) | 1.8 | 1.8 | 1.9 | 2.1 | 2.2 |
| Microbial Activity in Regenerating Vessel (nmol/min. · mg of microorganism) | 298 | 264 | 248 | 232 | 244 |
| Acetaldehyde Concentration in Regenerating Vessel (nmol/min. · mg of microorganism) | 0 | 0.26 | 0.64 | 0.72 | 0.74 |
| Amount of Acetaldehyde Produced (mol/hour) | — | 76 | 85 | 89 | 97 |

COMPARATIVE EXAMPLE 20

Example 79 was repeated, except that the scrubber was removed from the apparatus system of FIG. 2 with the reactor vessel being connected directly to the regenerating vessel, and neither methanol nor methane was supplied to the regenerating vessel. As a result, the amount of the acetaldehyde produced after 24 hours was at most 5 μmol/hour.

EXAMPLE 80

With the same apparatus system as used in Example 78, Example 78 was repeated, except that 1-butene was used in place of propylene. The results are set forth in Table 30.

TABLE 30

|  | Time (hour) Elapsed After Reaction Initiation | | | | | |
|---|---|---|---|---|---|---|
|  | 0 | 1 | 24 | 168 | 240 | 288 |
| Microbial Concentration in Reactor (mg/ml) | 2.1 | 2.0 | 2.3 | 2.4 | 2.3 | 2.3 |
| Microbial Activity in Reactor (nmol/min. · mg of microorganism) | 350 | 289 | 198 | 207 | 203 | 207 |
| Microbial Activity in Regenerating Vessel (nmol/min. · mg of microorganism) | 352 | 304 | 254 | 262 | 260 | 268 |
| Amount of 1,2-Butylene Oxide Produced (nmol/min. · mg of microorganism) | — | 1.98 | 1.62 | 1.72 | 1.58 | 1.68 |
| Butylene Oxide Concentration in Regenerating Vessel (mM) | 0 | 0.21 | 0.27 | 0.24 | 0.26 | 0.25 |

EXAMPLE 81

This example was carried out with the apparatus system shown in FIG. 1.

One point eight (1.8) liters of a medium obtained by mixing together the medium specified in Table 1 except that the concentration of $CuSO_4.5H_2O$ was changed to 1000 μg and the medium specified in Table 2 in a mixing ratio of 100:1.5 were charged into a regenerating vessel B of 24 liters in volume through a sterile filter.

On the other hand, 50 ml portions of a medium having the same composition, which had been treated through a sterile filter for the removal of infectious microbes, were charged into six Mayer's flasks of 500 ml in volume. One platinum loop of slant-cultured *Methylococcus capsulatus* NCIB 11132 was inoculated into each flask, which was then closed with a rubber plug, followed by pouring of 100 ml of methane. Culture was subsequently carried out at 45° C. for 3 days. The obtainted culture solution amounting to 300 ml in all was inoculated on the medium contained in the vessel B. While supplying a mixed methane/air gas of 1:4 at a rate of 1.35 liters per minute and carbon dioxide at a rate of 0.05 liter per minute to the vessel B, cultivation was carried out at 45° C. for 48 hours with shaking at 1,000 r.p.m. In consequence, the microbial concentration reached 0.7 mg/l.

Next, the microbial suspension was supplied to a reactor vessel A at a rate of 3 liters per hour by means of a pump 1. The amount of the solution contained in reactor A was controlled to 320 ml by means of a pump 3. The pump 3 was actuated to supply all the amount of the microbial suspension from the reactor A to the upper portion of a scrubber D and return it to the vessel B through the lower portion thereof. Next, the medium specified in Table 31 was supplied to the vessel B at a rate of 1.7 liters/hour, while air and methane were fed to the vessel B at the respective rate of 1.5 liters/min. and 0.27 liters/min. for agitation at 1,500 r.p.m. This condition was maintained for 24 hours.

TABLE 31

| | |
|---|---|
| Magnesium sulfate.7H$_2$O | 1.0 g |
| Potassium nitrate | 1.5 g |
| Calcium chloride | 20 mg |
| NaMoO$_4$ | 1 mg |
| FeSO$_4$.7H$_2$O | 500 μg |
| ZnSO$_4$.7H$_2$O | 400 μg |
| H$_3$BO$_4$ | 15 μg |
| CoCl$_2$.6H$_2$O | 50 μg |
| MnCl$_2$.4H$_2$O | 20 μg |
| NiCl$_2$.6H$_2$O | 10 μg |
| CuSO$_4$.5H$_2$O | 2000 μg |
| EDTA | 250 μg |
| Na$_2$PHO$_4$.12H$_2$O | 645 mg |
| KH$_2$PO$_4$ | 234 mg |
| Fe-EDTA | 7.2 mg |
| Distilled water | 1 liter |

After the microbial concentration had reached 2 mg/ml, the pump 2 was actuated to supply the suspension contained in the reactor A to the upper portion of a scrubber C at a rate of 120 ml per minute. At the same time, all the amount of the effluent gas of methane/air/carbon dioxide gas was guided to the lower portion of the scrubber D, and air was additionally fed at a rate of 2 l/min. from the lower portion of the scrubber D and all the amount of the effluent gas discharged through the upper portion thereof was guided to the lower portion of the scrubber C and discharged through the upper portion thereof. This condition was maintained for further 24 hours. The scrubbers C and D, reactor A and vessel B were all maintained at 45° C.

Subsequently, while propylene and air were supplied under agitation at 800 r.p.m. to the reactor A from the lower portion thereof at the respective rates of 230 ml/min. and 340 ml/min., 1M methanol solution was fed thereto at a rate of 8.5 mmol/hr. to initiate the reaction.

During that reaction, the reaction vessel and the regenerating vessel were controlled to pH 7.4 and 8.1, respectively, with 1M nitric acid. Extra microorganisms were discharged from the system to the outside to keep 18 liters of the amount of the solution contained in the regenerating vessel.

The effluent gas leaving the upper portion of the scrubber C was analyzed by mass spectrometer to determine the quantity of the propylene oxide produced. The results are set forth in Table 32.

TABLE 32

| | Time (hour) Elapsed After Reaction Initiation | | | | |
|---|---|---|---|---|---|
| | 0 | 1 | 7 | 17 | 27 |
| Microbial Concentration in Reactor (mg/ml) | 2.1 | 2.1 | 2.1 | 1.9 | 1.9 |
| Microbial Activity in Reactor (nmol/min. · mg of microorganism) | 452 | 426 | 416 | 442 | 414 |
| Microbial Activity in Regenerating Vessel (nmol/min. · mg microorganism) | 450 | 261 | 272 | 278 | 304 |
| Amounts of Propylene Oxide Produced (nmol/hour) | 0 | 8.7 | 8.9 | 8.8 | 8.8 |
| Amount of Propylene Oxide in Regenerating Vessel (mM) | 0 | 0.05 | 0.06 | 0.05 | 0.04 |

As set forth above, propylene oxide could stably be produced even after about 1 month.

COMPARATIVE EXAMPLE 21

The apparatus system was operated for 24 hours in a manner similar to that described in Example 8. However, the supply of methane to the regenerating vessel B was interrupted on the 29th day, and the supply of the regenerating solution (Table 31) to the regenerating vessel B was stopped. The results are set forth in Table 33.

TABLE 33

| | |
|---|---|
| Microbial Concentration in Reactor (mg/ml) | 1.7 |
| Microbial Activity in Reactor (nmol/min. · mg of microorganism) | 38 |
| Microbial Activity in Regenerating Vessel (nmol/min. · mg of microorganism) | 45 |
| Amount of Propylene Oxide Produced (nmol/hour) | <0.1 |
| Amount of Propylene Oxide in Regenerating Vessel (mM) | <0.01 |

We claim:

1. In a method for reactivating the methane oxidizability of microbial cells of a methane-utilizing bacteria which have partly or wholly lost their methane oxidizability, the improvement which comprises reactivating said methane-utilizing bacteria in an reactivation solution containing a carbon source selected from the group consisting of not less than 10 n mol/minute mg of cells methane, about 10 to 600 n mol/minute mg of cells methanol and about 10 to 600 n mol/minute mg of cells formaldehyde or a mixture thereof, while supplying thereto a not less than 1 n mol/minute mg of cells nitrogen source, a not less than 0.02 n mol/minute mg of cells sulfur source and oxygen.

2. A method as defined in claim 1, wherein said methane-utilizing bacteria belongs to any of the group of genera consisting of Methylococcus, Methylomonas, Methylosinus, Methylocystis, Methylobacterium and Methylobacter.

3. The method of claim 1, wherein the nitrogen source is used in an amount of 2-500 n mol/minute mg of cells.

4. The method of claim 3, wherein methane is used as the source of carbon.

5. The method of claim 4, wherein methane is used in an amount of not less than 30 n mol/minute mg of cells.

6. The method of claim 3, wherein methanol is used as the source of carbon.

7. The method of claim 6, wherein methanol is used in an amount of 30-400 n mol/minute mg of cells.

8. The method of claim 3 wherein formaldehyde; is used as the source of carbon.

9. The method of claim 8, wherein formaldehyde is used in an amount of 30-400 n mol/minute mg of cells.

10. The method of claim 3, wherein the sulfur source is used in an amount of 0.1-150 n mol/minute mg of cells.

11. The method of claim 3, wherein
the source of nitrogen is gaseous nitrogen, nitric acid, potassium nitrate, sodium nitrate, ammonium nitrate, ammonium sulfate, peptone, casaminoic acid, L-glutamine, or L-asparagine; and
the source of sulfur is sulfuric acid, magnesium sulfate, potassium sulfate, sodium sulfate, sodium sulfide, hydro sulfide or sodium sulfhydrate.

12. The method of claim 11, wherein
methane is used in an amount of not less than 30 n mol/minute mg of cells;
methanol and formaldehyde are used in an amount of 30-400 n mol/minute mg of cells; and
the sulfur source is used in an amount of 0.1-150 n mol/minute mg of cells.

13. The method as defined in claim 12, wherein said methane-utilizing bacteria belongs to any one of the group of genera consisting of Methylococcus, Methylomonas, Methylosinus, Methylocystis, Methylobacterium and Methylobacter.

14. The method of claim 2, wherein the bacteria are Methylococcus.

15. The method of claim 2, wherein the bacteria are Methylomonas.

16. The of method claim 2, wherein the bacteria are Methylosinus.

17. The method of claim 2, wherein the bacteria are Methylocystis.

18. The method of claim 2, wherein the bacteria are Methylobacterium.

19. The method of claim 2, wherein the bacteria are Methylobacter.

* * * * *

UNITED STATES PATENT AND TRADEMARK OFFICE
CERTIFICATE OF CORRECTION

PATENT NO. : 5,013,665

DATED : May 7, 1991

INVENTOR(S) : SUZUKI et al

It is certified that error appears in the above-identified patent and that said Letters Patent is hereby corrected as shown below:

Title page, left column, below Section [22], insert the following:

--[30] Foreign Application Priority Data

November 30, 1987 [JP] Japan......62/302584
December 17, 1987 [JP] Japan......62/319832
December 17, 1987 [JP] Japan......62/319833
December 17, 1987 [JP] Japan......62/319834
May 27, 1988 [JP] Japan......63/128242--.

Column 3, line 40, replace ".mg" with --·mg--.

Column 3, line 41, replace ".mg" with --·mg--.

Column 3, line 50, replace ".mg" with --·mg--.

Column 3, line 53, replace ".mg" with --·mg--.

Column 3, line 60, replace ".mg" with --·mg-- (two occurrences).

Column 4, line 3, replace ".mg" with --·mg--.

Column 4, line 10, replace ".mg" with --·mg--.

Column 4, line 11, replace ".mg" with --·mg--.

Column 4, line 20, replace ".mg" with --·mg--.

UNITED STATES PATENT AND TRADEMARK OFFICE
CERTIFICATE OF CORRECTION

PATENT NO. : 5,013,665
DATED : May 7, 1991
INVENTOR(S) : SUZUKI et al

It is certified that error appears in the above-identified patent and that said Letters Patent is hereby corrected as shown below:

Column 4, line 21, replace ".mg" with ---·mg---.

Column 5, line 16, replace ".mg" with ---·mg---.

Column 5, line 17, replace ".mg" with ---·mg---.

Column 7, line 66, replace ".mg" with ---·mg---.

Column 9, line 40, replace ".mg" with ---·mg---.

Column 9, line 45, replace ".mg" with ---·mg---.

Column 9, line 47, replace ".mg" with ---·mg---.

Column 9, line 49, replace ".mg" with ---·mg---.

Column 9, line 50, replace ".mg" with ---·mg---.

Column 10, line 19, replace ".mg" with ---·mg---.

Column 10, line 20, replace ".mg" with ---·mg---.

Column 10, line 50, replace ".mg" with ---·mg---.

Column 15, line 40, replace ".mg" with ---·mg---.

Column 16, line 54, replace ".mg" with ---·mg---.

Column 18, line 20, replace ".mg" with ---·mg---.

UNITED STATES PATENT AND TRADEMARK OFFICE
CERTIFICATE OF CORRECTION

PATENT NO. : 5,013,665

DATED : May 7, 1991

INVENTOR(S) : SUZUKI et al

It is certified that error appears in the above-identified patent and that said Letters Patent is hereby corrected as shown below:

Column 26, line 23 (Claim 1), replace "mol/minute mg" with
--mol/minute.mg--.

Column 26, line 24 (Claim 1), replace "mol/minute mg" with
--mol/minute.mg--.

Column 26, line 25 (Claim 1), replace "mol/minute mg" with
--mol/minute.mg--.

Column 26, line 27 (Claim 1), replace "mol/minute mg" with
--mol/minute.mg--.

Column 26, line 28 (Claim 1), replace "mol/minute mg" with
--mol/minute.mg--.

Column 26, line 36 (Claim 3), replace "mol/minute mg" with
--mol/minute.mg--.

Column 26, line 41 (Claim 5), replace "mol/minute mg" with
--mol/minute.mg--.

Column 26, line 45 (Claim 7), replace "mol/minute mg" with
--mol/minute.mg--.

Column 26, line 49 (Claim 9), replace "mol/minute mg" with
--mol/minute.mg--.

Column 26, line 51 (Claim 10), replace "mol/minute mg" with
--mol/minute.mg--.

UNITED STATES PATENT AND TRADEMARK OFFICE
CERTIFICATE OF CORRECTION

PATENT NO. : 5,013,665

DATED : May 7, 1991

INVENTOR(S) : SUZUKI et al

It is certified that error appears in the above-identified patent and that said Letters Patent is hereby corrected as shown below:

Column 26, line 64 (Claim 12), replace "mol/minute mg" with --mol/minute.mg--.

Column 26, line 66 (Claim 12), replace "mol/minute mg" with --mol/minute.mg--.

Column 26, line 68 (Claim 12), replace "mol/minute mg" with --mol/minute.mg--.

Signed and Sealed this

Sixth Day of December, 1994

Attest:

BRUCE LEHMAN

*Attesting Officer*    *Commissioner of Patents and Trademarks*